United States Patent [19]

Azuma

[11] Patent Number: 4,849,178
[45] Date of Patent: Jul. 18, 1989

[54] APPARATUS FOR MEASURING OZONE CONCENTRATION

[75] Inventor: Kenkoku Azuma, Nagoya, Japan

[73] Assignee: Mitsubishi Denki Kabushiki Kaisha, Japan

[21] Appl. No.: 396,175

[22] Filed: Jul. 7, 1982

[30] Foreign Application Priority Data

Jul. 8, 1981 [JP] Japan .................................. 56-106350

[51] Int. Cl.$^4$ ............................................. G01N 21/59
[52] U.S. Cl. ...................................... 422/69; 73/61 R; 422/68; 436/135; 436/164; 436/177
[58] Field of Search .................. 55/256; 210/749, 750, 210/760; 261/DIG. 42; 422/52, 55, 68, 69; 436/135, 164, 167, 172, 175, 177; 73/61 R

[56] References Cited

U.S. PATENT DOCUMENTS

| 2,417,321 | 3/1947 | Park et al. ........................ 436/164 X |
| 3,528,779 | 9/1970 | Fontyn ............................... 436/135 |
| 3,967,933 | 7/1976 | Etess et al. ...................... 436/172 X |
| 4,240,799 | 12/1980 | Ryerson ............................. 436/135 |
| 4,256,710 | 3/1981 | Azuma et al. ..................... 422/4 X |
| 4,269,057 | 5/1981 | Ong et al. .......................... 422/83 X |
| 4,353,717 | 10/1982 | Herbrechtsmeier et al. ... 210/760 X |

FOREIGN PATENT DOCUMENTS

| 0029793 | 3/1977 | Japan ..................................... 422/68 |
| 0129752 | 10/1980 | Japan ................................... 436/135 |
| 0941275 | 7/1982 | U.S.S.R. ............................... 436/135 |

OTHER PUBLICATIONS

Arora et al, Indian Journal of Technology, vol. 15, pp. 528–530, (Dec. 1977),
Ardzhanov et al, Measurement Techniques, vol. 19, #5, pp. 743–745, (May 1976).

*Primary Examiner*—Robert J. Hill, Jr.
*Attorney, Agent, or Firm*—Sughrue, Mion, Zinn, Macpeak & Seas

[57] ABSTRACT

An apparatus for measuring ozone concentration in which ozone contained in a liquid to be measured is caused to shift into a clean gas in a gas-liquid contacting tube. The gas into which the ozone has shifted is supplied to a photocell into which light is projected. The gas supplied to the photocell is exhausted through an ozone dissolving tube. The light transmitted through the photocell enters a detector. The output from the detector is utilized as an indication of the concentration of ozone in the exhausted gas, and hence in the liquid.

5 Claims, 1 Drawing Sheet

APPARATUS FOR MEASURING OZONE CONCENTRATION

BACKGROUND OF THE INVENTION

The present invention relates to an apparatus for measuring ozone concentration, and more particularly to an apparatus for measuring the concentration of ozone dissolved in a liquid.

A conventional apparatus of the general type to which the invention pertains is shown in FIG. 1.

A pump 1 supplies ozone-containing liquid to a mixing tube 4 at a predetermined constant rate through a pipe 11, and a pump 2 supplies the mixing tube 4 an aqueous solution of potassium iodide at a predetermined constant rate from a tank 3 to be mixed with the ozone-containing liquid.

A photocell 5 receives the mixed liquid from the mixing tube 4. A light source 6 is provided at one side of the photocell 5 for projecting light into the photocell 5 through an optical filter 7. A detector 8 is provided on the side of photocell 5 opposite the light source 6 for detecting or analyzing the concentration of the ozone contained in the mixed liquid. An electrical transmission channel 10 is provided between the detector 8 and a recorder 9 which records the transmitted data.

The operation of the apparatus described above is as follows.

The ozone-containing liquid supplied by pump 1 is uniformly mixed with the potassium iodide (KL) aqueous solution in the mixing tube 4. The ozone contained in the liquid reacts with the potassium iodide (KL) to produce iodine ($I_2$) according to the reaction:

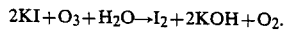

$$2KI + O_3 + H_2O \rightarrow I_2 + 2KOH + O_2.$$

The iodine ($I_2$) thus produced has a light absorption spectrum for which the maximum light absorption coefficient occurs in the vicinity of a wavelength of 560 nm. The concentration of the ozone is measured continuously by measuring the amount of light absorption in the vicinity of this wavelength with the photocell 5.

In the conventional type ozone measuring apparatus utilizing the reaction between ozone ($O_3$) and potassium iodide, when the liquid to be measured contains components other than ozone which can react with potassium iodide (KI) to produce iodine ($I_2$), for example, oxidizing chlorides ($ClO^-$, $HClO$), nitrate ion ($NO_3^-$), ferric ion ($F^{3+}$), etc., it is difficult to measure the concentration of ozone precisely.

In particular, chlorine is usually added as an oxidizer to disinfect ordinary tap water. Consequently, if tap water is used, the influence of chlorine contained therein on the measurement of the concentration of ozone in water or another liquid is unavoidable.

SUMMARY OF THE INVENTION

It is accordingly an object of the invention to provide an apparatus for precisely measuring the concentration of ozone contained in a liquid without the measurement being affected by components which may be present with the ozone in the liquid under measurement.

The foregoing and other objects of the invention have been attained by providing an apparatus for measuring the concentration of ozone contained in a liquid comprising a gas-liquid contacting means which is supplied with ozone-containing liquid at a first predetermined rate and a clean gas at a second predetermined rate and which contacts the liquid and the gas. Optical means is supplied with the gas into which said ozone contained in the liquid has shifted in the gas-liquid contacting means. Light of an appropriate wavelength is shone onto the optical means. The light transmitted through the optical means is detected to determine the concentration of ozone in the gas, and hence in the liquid.

DESCRIPTION OF THE PREFERRED EMBODIMENTS

Figure 1:
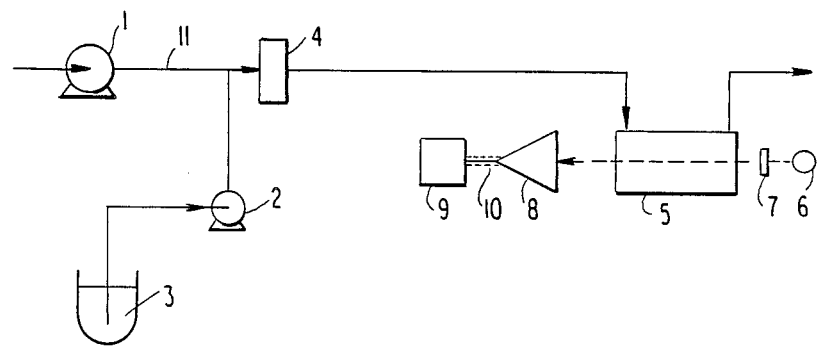
FIG. 1 shows a conventional apparatus for measuring an ozone concentration.
Figure 2:
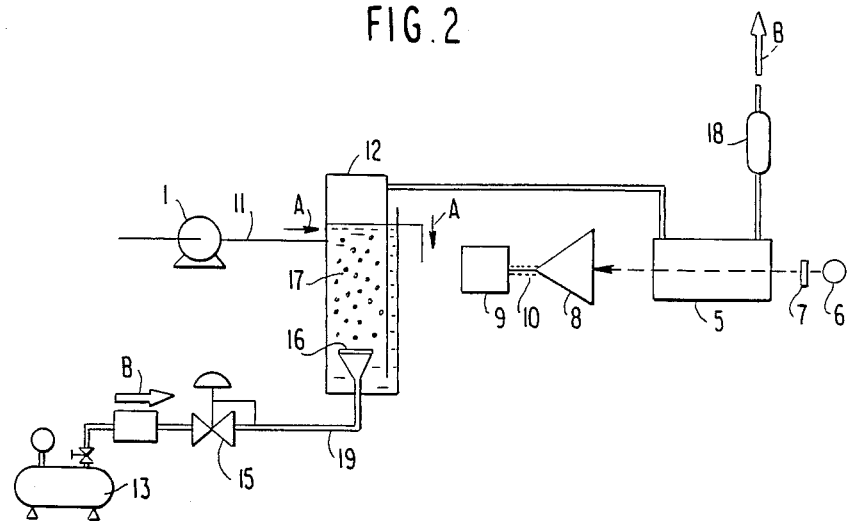
FIG. 2 shows an apparatus for measuring an ozone concentration of the present invention.

In FIG. 2, which shows a preferred embodiment of an apparatus for measuring an ozone concentration constructed in accordance with the invention, reference numerals which are the same as those found in FIG. 1 designate similar or corresponding parts to those indicated by the same numerals in FIG. 1.

Reference numeral 12 designates a gas-liquid contacting tube to which the ozone-containing liquid and clean air are supplied and in which the liquid and gas are contacted with each other. Clear air from a compressor 13 passes to a diffuser 16 through a filter 14, reduction pressure valve 15, and feed pipe 19. At the outlet side of the photocell 5, a dissolving tube 18 is connected which contains an ozone dissolving element such as activated charcoal, nickel oxide, etc. In FIG. 2, arrows A and B indicate the direction of flow of the liquid to be measured and that of the clean air.

For the pump 1, which supplies the liquid to be measured, it is preferred to use a so-called oilless type, which prevents oil from entering the liquid. Also, it is preferable that the components of the pumps which contact the liquid be made of a material not corroded by ozone, such as stainless steel, polyvinyl chloride, glass, or fluorine-containing polymers.

With respect to the pipe 11, contacting tube 12, photocell 5 and dissolving tube, all the components thereof which contact the ozone-containing liquid and air should be made of a material similar to that of the components of the pump 1 contacting the ozone-containing liquid and air. A filter of the general dust collecting type is to be used for the filter 14.

The operation of this embodiment of the invention is described below.

The liquid to be measured is supplied by pump 1 at a first predetermined constant rate to the gas-liquid contacting tube where the liquid contacts the clean air. This contact makes the ozone shift into the clean air. The clean air containing the ozone then is supplied to the photocell 5.

Ozone has an intense absorption spectrum for ultraviolet light at wavelengths in the range of 210–300 nm. The absorption coefficient at the peak absorption wavelength of 265 nm reaches about 130 cm$^{-1}$ near room temperature. By measuring with the detector 8 (which may be a phototube or a transistor photodetector) the amount of light from the light source 6 (which may be a low pressure mercury lamp functioning as an ultraviolet light source) transmitted through the photocell 5, it is possible to measure the concentration of the ozone in the clean air supplied to photocell 5.

Ozone is rather insoluble in water. For instance, Henry's constant at 20° C. is $3.75 \times 10^3$ atoms/mole. Hence, contacting the ozone-containing liquid with air makes the ozone easily shift into the air.

With L (l/min) being the rate at which ozone-containing liquid is supplied to the contact tube, C (ppm) the ozone concentration, G (l/min at 0° C. 1 atm, hereinafter Nl/min) the rate at which clean air is supplied to the contacting tube, and P (ppm) the concentration of the ozone in the air after contact with the liquid, the following equation relates P and C:

$$(G/22.4) \times P \times 10^{-6} = 10^3 L \times C \times 10^{-6}/48,$$

$$P = 467 \, CL/G.$$

Therefore, assuming C=1 ppm, L=1 l/min, and G=1 Nl/min, the value of P is 467 ppm.

It should be noted that nitride ion ($NO_3^-$) and ferric iron ($F^{3+}$), etc., which may be present in tap water, are rather highly water soluble. Since the concentrations thereof are ordinarily less than 1-10 ppm, they will not shift into the air in contact with the ozone-containing liquid and hence will not adversely affect the measurement.

Contrarily, iodine ($I_2$) partially shifts into the air in the form of anhydrous hypochlorous acid ($Cl_2O$), but the influence on the measured value of the ozone is negligible. The reason for this is as follows. In the case where the concentration of iodine ($I_2$) in the liquid is 1 ppm, the concentration of iodine shifting into the air in the form of anhydrous hypochlorous acid ($Cl_2O$) is small, that is, less than 0.1 ppm, such that the amount of light absorption in the vicinity of 265 nm is only about one hundredth that of ozone.

Specific numerical values for the described process, and further details of this process will now be given.

In the embodiment shown in FIG. 2, the liquid to be measured is supplied to the contacting tube 12 at a rate such that the liquid remains in the contacting tube longer than one minute. For example, if the rate of supply of the liquid is 1 l/min, then the effective volume of the contacting tube 12 should be more than 1 l.

Generally, the rate of supply of the liquid is determined taking into account both the reaction rate for measuring ozone concentration and the capacity of the pump 1, and may typically be selected within a range of from 0.1 l/min to 10 l/min.

The rate at which clean air is supplied is selected so that the liquid is prevented from being splashed out of the contacting tube 12 together with the ozone-containing air. In the specific case under discussion, the flow speed of the clean air into the tube 12 is selected to be less than 0.5 m³/min but high enough so that all of the ozone contained in the liquid can shift into the air.

In general, the rate of supply of air is selected to be more than twice the minimum value which enables all of the ozone in the liquid to shift into the air. Under the condition that the quantity of liquid to be measured is 1 l/min, the liquid temperature is 20° C., and the cross-sectional area of the contacting tube is 100 cm², and the ascending speed of the clean air within the vacant contacting tube is 50 cm/min, the maximum flow rate $G_{max}$ of the clean air to be contacted with the ozone-containing liquid is given by the equation:

$$G_{max} = 100 \text{ cm}^2 \times 50 \text{ cm/min} = 5 \text{ l/min}.$$

The minimum flow rate $G_{min}$ of the clean air is calculated as follows. Taking C as the concentration of the ozone contained in the liquid, H (atm/molar ratio) as Henry's constant, and assuming that all of the ozone [($1 \times C \times 10^{-3}/48$) mol/min] contained in the liquid shifts into the clean air [($G_{min}/22.4$) mol/min] by contacting the air, the concentration of the ozone contained in the clean air after contact is:

$$\frac{1 \times C \times 10^{-3}/48}{G_{min}/22.4} = 4.87 \times 10^{-4} \, C/G_{min} \text{ mol/mol}.$$

Since $G_{min}$ can be obtained by assuming the partial pressure of the ozone contained in the air contacted with the liquid to be equal to an equilibrium backpressure of ozone having a concentration C in the liquid, taking 1 atm as the total pressure of the air contacting the liquid, the following equation is derived:

$$\frac{1 \times 4.67 \times 10^{-4}C}{1 \times 4.67 \times 10^{-4}C + G_{min}} = H \times \frac{C \times 1 \times 10^{-3}/48}{1000/18}.$$

In this equation, as $G_{min} >> 1 \times 4.67 \times 10^{-6}C$, $$G_{min} = 1245/H \text{ Nl/min}.$$

At a temperature of 20° C., $G_{min}$ is 0.33 Nl/min. Consequently, the quantity of air supplied to the contacting tube in order to properly contact it with the ozone-containing liquid may be selected as follows:

$$2 \times 0.33 \leq G \leq 5 \text{ Nl/min}.$$

With regard to the relationship between the effective optical path and the quantity of light entering the detector, details thereof will now be described.

In an example where a low pressure mercury lamp is used for the light source, the rate L at which the liquid supplied to the contacting tube 12 is 1 l/min, the rate G at which the air is supplied to the contacting tube 12 is 1 Nl/min, and the maximum concentration of ozone contained in the liquid is assumed to be $C_{max}$ (ppm), the variation $\Delta I$ of the quantity of light entering the detector 8 due to the presence of ozone is given by the following equation:

$$\frac{\Delta I}{I_o} = 10^{-467 C_{max} \times 10^{-6} \times 130 L^*}.$$

In this equation, $L^*$ is the effective optical length of the photocell 5 and $I_o$ is the quantity of light which enters the detector 8 when the ozone concentration is zero. From this equation, it may be seen that if the effective optical length $L^*$ of the photocell 5 is selected to be $11.5/C_{max}$, $\Delta I/I_o$ is nearly equal to 0.2.

In the embodiment of the invention described above, the contacting tube 12 is of a type in which bubbles of a clean gas contact ozone-containing liquid, and the clean gas is clean air. It is also possible to use, as the contacting tube 12, a contacting tube of a spray type in which the ozone-containing liquid is sprayed. It is further possible to use as the clean gas contacting the liquid, nitrogen, argon, helium, or oxygen in a high pressure cylinder.

Additionally, it is possible to detect the concentration of ozone in the gas after contact with the liquid by measuring the luminescent intensity of the light which is produced in a chemical reaction between the ozone and such added hydrocarbons as ethylene. In the case of measuring the ozone concentration using a hydrocarbon supplied to the photocell instead of projecting light as in the first-described embodiment, nitrogen oxide (NO) can be substituted for the hydrocarbons of the ethylene series.

As described above, according to an apparatus of the present invention, ozone contained in a liquid supplied at a first predetermined constant rate make contact with a clean gas supplied at a second predetermined constant rate and shifts from the former into the latter. Because the concentration of the ozone contained in the gas can be accurately measured and because the concentration of ozone in the gas can be accurately related to that in the liquid, consequently the influence of iodine, nitrate radicals, or heavy metal ions which may exist in the ozone-containing liquid, which had plagued prior art approaches, is eliminated. Accordingly the apparatus of the invention provides a more precise measurement of the concentration of ozone contained in a liquid than has hitherto been possible.

I claim:

1. An apparatus for measuring the ozone concentration of a liquid, comprising:
    a gas-liquid contacting means which is supplied with an ozone-containing liquid at a first predetermined rate and a clean gas at a second predetermined rate for contacting said liquid with said gas, to thereby shift the ozone in said liquid to said gas;
    optical analyzing means which is supplied with the gas exhausted from said contacting means,
    said analyzing means including a light source outputting light of a frequency normally absorbed by the ozone present in said exhaust gas, and means for measuring the amount of ozone present in said ozone-containing liquid by sensing the amount of said light passing through said exhausted gas.

2. The apparatus for measuring ozone concentration according to claim 1, wherein said gas-liquid contacting means comprises a diffuser for diffusing said clean gas into said ozone-containing liquid.

3. The apparatus for measuring ozone concentration according to claim 1, wherein said clean gas is supplied to said gas-liquid contacting means by a compressor of an oilless type.

4. The apparatus for measuring ozone concentration according to claim 1, further comprising an ozone dissolving tube for exhausting said ozone-containing gas supplied to said optical means.

5. An apparatus for measuring the ozone concentration of a liquid, comprising;
    means for receiving an ozone-containing liquid at a first predetermined rate and a clean gas at a second predetermined rate, and for shifting the ozone in said ozone-containing liquid to said clean gas, by contacting said ozone-containing liquid with said clean gas;
    optical analyzing means which is supplied with the gas exhausted from said shifting means;
    said analyzing means including a light source outputting light of a frequency normally absorbed by the ozone present in said exhaust gas, and means for measuring the amount of ozone present in said ozone-containing liquid by sensing the amount of said light passing through said exhausted gas.

* * * * *